United States Patent [19]

Hardy et al.

[11] Patent Number: 4,722,225
[45] Date of Patent: Feb. 2, 1988

[54] ULTRASONIC INSPECTION SYSTEM

[75] Inventors: Robert B. Hardy; Charles D. Richards, both of Simi Valley; Paul H. Waite, Palmdale, all of Calif.

[73] Assignee: Rockwell International Corporation, El Segundo, Calif.

[21] Appl. No.: 818,294

[22] Filed: Jan. 10, 1986

[51] Int. Cl.⁴ ............................................. G01N 29/04
[52] U.S. Cl. ........................................ 73/622; 73/633; 73/635
[58] Field of Search ................. 73/622, 634, 637, 638, 73/661, 633, 635

[56] References Cited

U.S. PATENT DOCUMENTS

| | | | |
|---|---|---|---|
| 3,190,112 | 6/1965 | Beaujard et al. | 73/635 |
| 3,552,190 | 1/1971 | Lefebvre | 73/622 |
| 3,857,052 | 12/1974 | Beller | 340/149 R |
| 3,982,425 | 9/1976 | McLain | 73/67.8 S |
| 4,545,570 | 10/1985 | KaDell, Jr. | 269/52 |
| 4,612,808 | 9/1986 | McKirdy et al. | 73/622 |

*Primary Examiner*—Anthony V. Ciarlante
*Attorney, Agent, or Firm*—H. Fredrick Hamann; Harry B. Field; David C. Faulkner

[57] ABSTRACT

An ultrasonic inspection system for performing in-service inspection of atomic reactors and the like includes a remote inspector including a transducer holding device of novel design and function. The holding device basically comprises an outer housing; an inner housing rotatably retained within said outer housing; an ultrasonic transducer retained within said inner housing; retention means for selectively positioning said transducer within said inner housing; and means for locking said transducer within said inner housing at a selected position.

4 Claims, 5 Drawing Figures

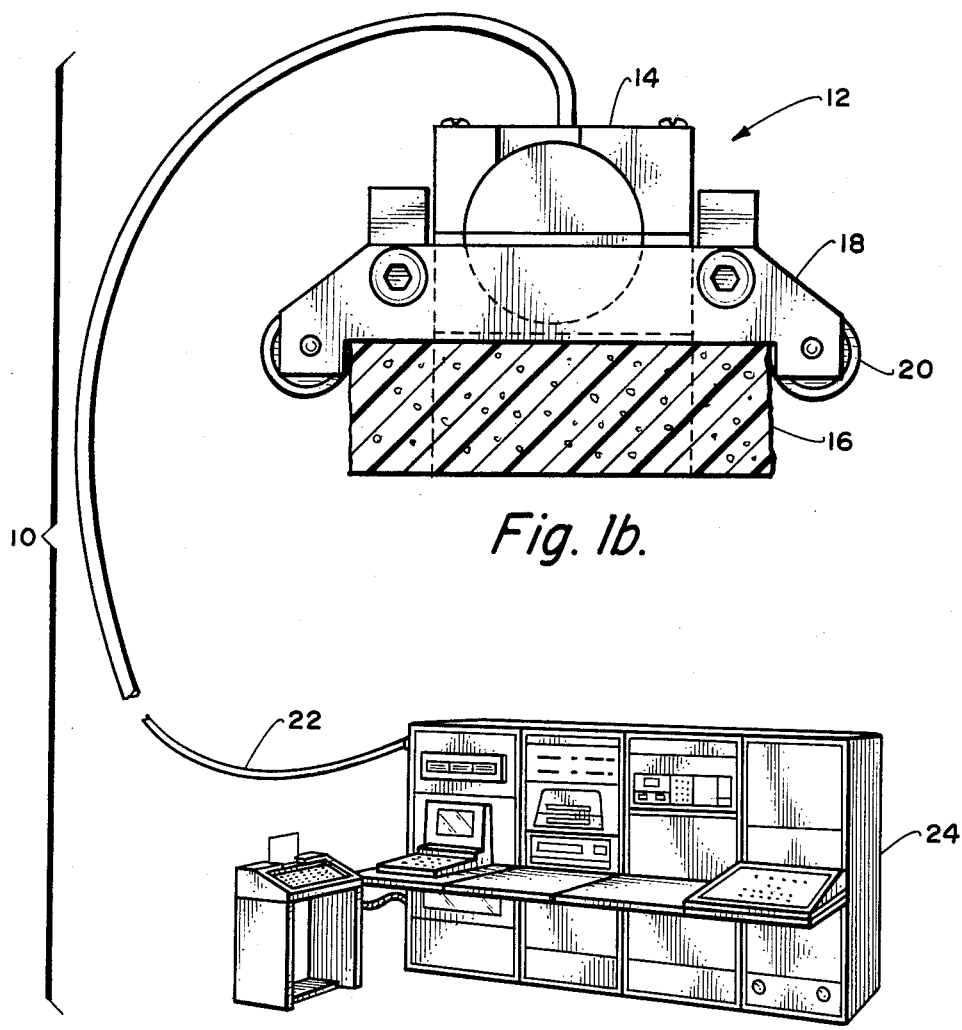
Fig. 1b.
Fig. 1a.
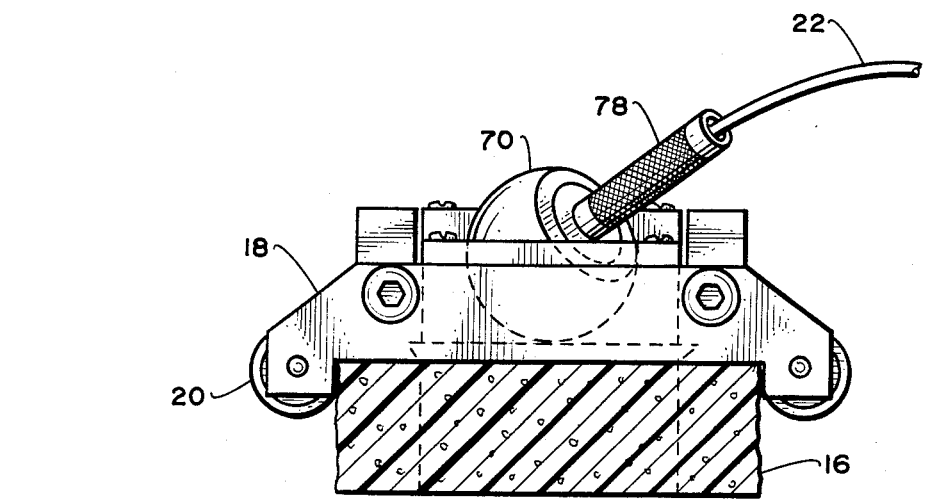
Fig. 4.

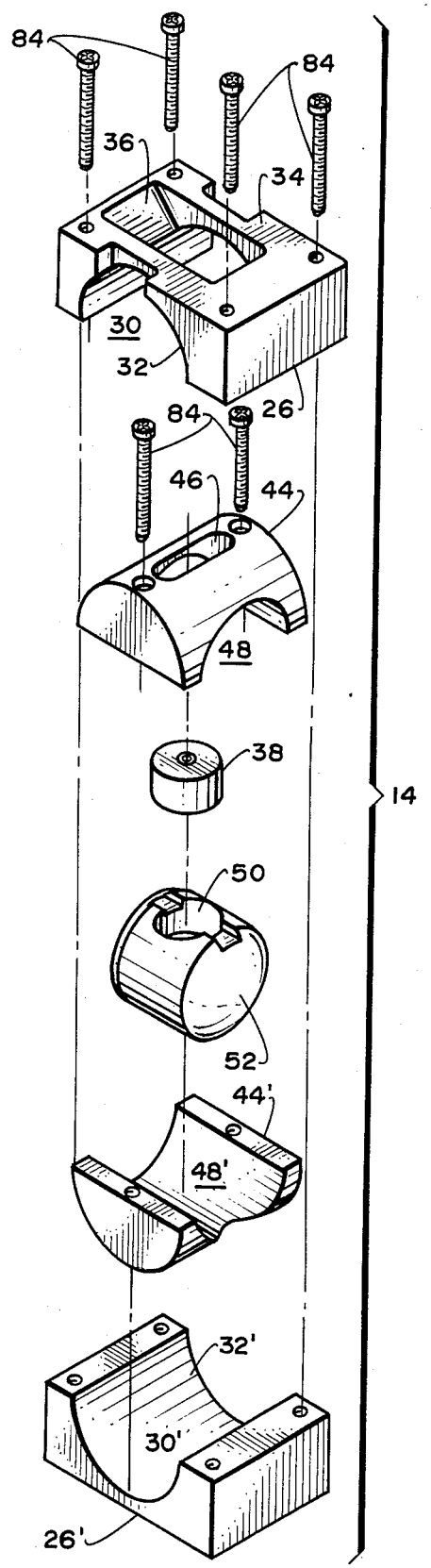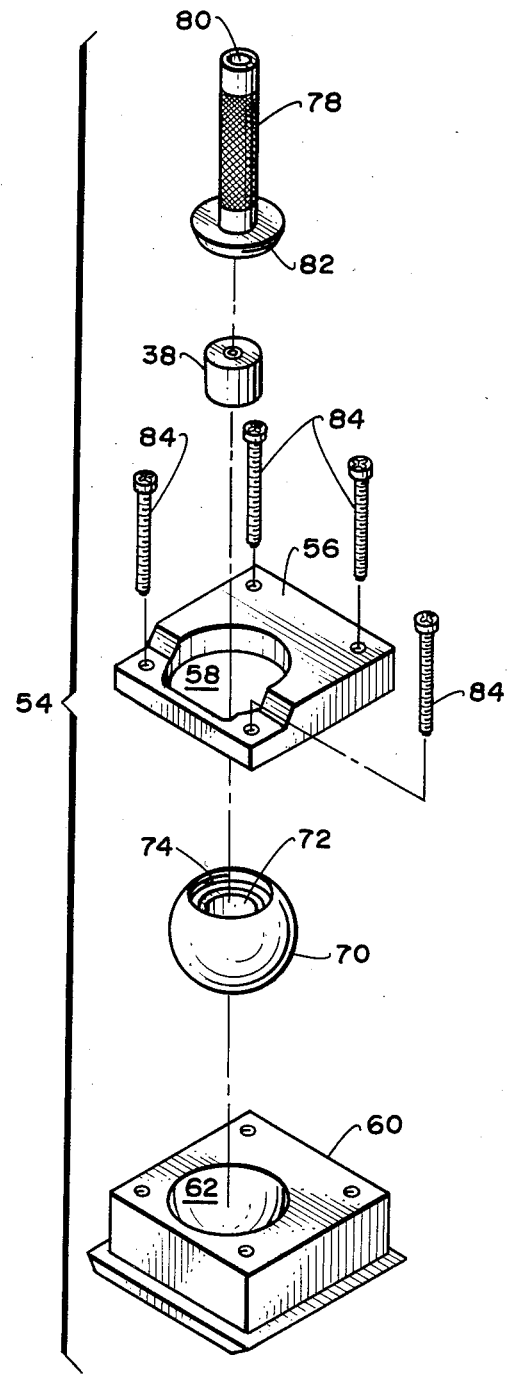
Fig. 2.
Fig. 3.

ULTRASONIC INSPECTION SYSTEM

BACKGROUND OF THE INVENTION

1. Field of the Invention

The invention relates to ultrasonic inspection systems, and is particularly directed to a remote inspector including a holding device for performing in-service inspection of atomic reactors and the like.

2. Description of the Prior Art

Ultrasonic in-service inspection systems have been developed in the recent past for fast breeder reactors and both pressurized and boiling-water reactors. The technical approach which has been followed features remotely controlled traveling instrument carriers (a remote inspector), and computerized collection and storage of inspection data in a manner providing real-time comparison against predetermined standards. Numerous types of equipment have been proposed, heretofore, for accomplishing such inspections. However, none of the prior-art inspection systems have been entirely satisfactory. Inspection of reactor vessels and like equipment must be carried out to meet fully the intent of Section XI of the American Society of Mechanical Engineering (ASME) Boiler and Pressure Vessel Code.

In many presently utilized ultrasonic inspection systems, a computer controlled remote inspector or instrument carrier (commonly referred to as a "skate") is provided with only enough structure to permit positioning the skate along a track adapted to fit the specific contour of the steam generator, reactor vessel, and the like, to be inspected. The details of one such skate and track, and a method of mounting the track are disclosed in U.S. Pat. No. 3,857,052 assigned to the assignee of this application and incorporated herein by reference.

In order to minimize the size and weight of the remote inspector or skate, only the piezoelectric transducer holding device of the ultrasonic inspection system is mounted on the remote inspector. A transducer is connected to the main control console through a flexible transmission line. The transducer is then periodically pulsed under control of the computer through the transmission line, and echoes sent by the transducer following each pulse are carried back to the main computer console through the same transmission line.

In those systems the transducers are mounted on slider shoes or wheels that are attached to the remote inspector, which moves on the surface of the subject being examined. Vertical, horizontal, and rotational motion of the inspector is provided, and the position is determined by encoders that return this information to the computer.

In accordance with the requirements of the ASME Code, the ultrasonic waves are transmitted at various angles through the subject surface. The current code calls for normal incidence, 45° from normal, and 60° from normal. The 45° and 60° angles are used to detect planar flaws located parallel or transverse to the surface. A 90° or straight-beam is used to detect laminar-type indications and, at high gain settings, planar types.

One such remote inspector or skate presently in use utilizes five transducers installed at various angles. This provides the capability for making a complete inspection (nine view angles) in one pass.

The ASME Code requires inspection, for example, at a number of angles which, if multiple transducers were not used would require multiple passes resulting in longer inspection times. The utilization of a multiple transducer equipped remote inspector necessitates a holding device or remote inspector of increased size and complexity.

BRIEF SUMMARY AND OBJECTIVES OF THE INVENTION

Accordingly, the present invention overcomes the disadvantages of the prior art by providing an inspection system which is completely automatic and includes a remote inspector including a transducer holding device of novel design and function.

The advantages of the present invention are preferably attained by providing an inspection system comprising a remote inspector for performing an inspection operation; positioning means supporting said remote inspector and operable to position said inspector with regard to a vessel to be inspected; an analog-to-digital converter connected to receive analog signals from said inspector and serving to convert said analog signals to digital signals.

The remote inspector itself comprises a holding device for an ultrasonic transducer, positioning and retaining means for mounting the holding device on a volume element of a wall or other structural member; all coupled to the aforesaid control and data acquisition console or analog-to-digital converter.

In simplified form, the system works as follows for a typical automatic ultrasonic inspection. The operator starts by adjusting the remote inspector and holding device housing a transducer according to project requirements. The computer is programmed with basic information, such as date, weld number, mode of inspection, equipment serial numbers, etc. With preprogrammed information, the computer moves the remote inspector to a beginning location and starts accepting ultrasonic data.

The data are obtained, analyzed, and presented to the inspector as the inspection proceeds.

Accordingly, it is an object of the present invention to provide an improved inspection system.

Another object of the invention is to provide an inspector unit in which a liquid filled skirt is employed to assure a reliable signal path between a transmitting and receiving transducer holding device and a structure being inspected.

Still another object of the invention is a holding device for housing an ultrasonic transducer in the remote inspector.

Another object of the invention is the provision for selectively positioning a transducer retained within the holding device and for locking the transducer within the selected position.

These and other objects and features of the present invention will be apparent from the following detailed description, taken with reference to the accompanying drawing. The same elements or parts throughout the figures of the drawings of designated by the same reference characters, while equivalent elements bear a prime designation.

BRIEF DESCRIPTION OF THE DRAWINGS

FIGS. 1a and 1b represent isometric views of an inspection system embodying the present invention;

FIG. 2 is an exploded view of one embodiment of a holding device according to the invention; and FIG. 3 is an exploded view of another embodiment of a holding device according to the present invention.

FIG. 4 is a partial isometric view of the holding device shown in FIG. 3.

DESCRIPTION OF THE PREFERRED EMBODIMENTS

Referring to the drawings, FIGS. 1a and 1b show an automated ultrasonic inspection system 10 comprising a remote inspector 12 including an ultrasonic transducer holding device 14. The holding device is also provided with a liquid-filled foam skirt 16 carried by skate 18 having wheels 20 driven by a motor (not shown). The motor causes skate 18 to carry the remote inspector along a predetermined path to inspect a wall of a reactor vessel, or the like, or some other structural member, such a steel structure of a bridge, where periodic in-service inspection is required. With this configuration, it is not feasible to carry more of the inspection system electronics on the skate than the remote inspector. In such a case it is necessary to connect the remote inspector to the rest of the automated ultrasonic inspection system by a transmission line such as a coaxial cable 22, included in a series of electrical lines. The remote inspector is operated remotely from the console or control and data acquisition system 24. Position sensors or encoders (not shown) are utilized to indicate the exact location of the remote inspector in terms of X-Y coordinates in relation to a reference point on the surface being inspected. As the skate moves the holding device along an inspection path, in response to computer controlled signals over a separate line in the circuitry connected to the motor, ultrasonic inspection information is received at the inspection console.

Referring now to FIG. 2, a holding device 14 for an ultrasonic transducer, utilized in a remote inspector, includes outer opposing generally rectangular sections 26 and 26' comprising an outer housing. A concave cylindrical recess 30 and 30' is machined into an inner surface 32 and 32' of each outer housing section. The outer surface or top 34 of one of said rectangular sections of the outer housing is provided with an access slot 36 for providing an electrical connection to a transducer 38. When assembled, these recesses oppose each other to form a spherical shaped bore. Within this bore is retained an inner housing comprising an outer cylindrical section formed by top and bottom semi-circular members 44 and 44'; the top semi-circular member is also provided with an electrical access slot aligned with said outer housing access slot. When joined together the resulting cylindrical section is rotatably retained or mounted within the cylindrically shaped bore of the outer housing. As shown, each member is provided with a concave semi-circular recess 48 and 48' formed at a 90° angle in relation to the cylindrical recess of the outer housing. A slotted recess 50 for receiving and retaining a transducer 38 is provided in a unitary inner cylindrical section 52 located within the bore formed when the semi-circular members are joined together during assembly of the holding device. Since the inner housing and the inner cylindrical section are independently rotatable, any desired transducer position within an arc of about 180° is readily obtainable.

As shown in FIG. 3, another embodiment of a holding device 54 according to the present ivention includes outer and inner housing elements. The outer housing comprises a pair of cuboidal sections; one designated upper section 56, which is provided with a semicircular channel or port 58. The second or lower cuboidal section 60 is provided with a hemispherical recess 62. Upon joining these sections a semicircular bore is formed such that the bore provides a communicative passageway between said port 58 and said recess 62.

An inner housing for retaining an ultrasonic transducer comprises a ball-shaped member or section 70 having a radially oriented socket-shaped recess 72 including a threaded wall 74 machined in the outer perimeter thereof. This recess receives and retains transducer 38. The inner housing 70 is configured so as to be rotatably seated within recess 62. A removable toggle 78 having an electrical wiring access 80 therethrough is provided having a threaded retainer end section 82 which is mated with and frictionally retained by the threaded wall 74 of recess 72. Once the threaded retainer end section 82 is positioned in wall 74, the toggle is used to rotatably position the ball-shaped member 70. This positions the transducer at a predetermined inspection angle. Then, the toggle is disconnected from the threaded end section 82 and removed simply by sliding the toggle along the electrical connection line 22 shown in FIG. 4, away from the remote inspector assembly.

In the embodiments shown in the Figures and as previously described, it is to be understood that the holding devices are preferably constructed of a polymeric material such as "Lucite" (Trademark of Enjay Chemical Co., Division of Humble Oil & Refining Co., New York, N.Y.). The sections or components forming each holding device and transducer element prepositioned therein, are assembled utilizing conventional means such as screws 84 (see FIGS. 2 and 3) and the like. It is to be understood that when using the term "assembled", the components including the ultrasonic transducer holding element, comprising the holding device are initially prepositioned. Final tightening of the holding or securing means (screws and the like) serve to lock in place the prepositioned components of the holding device. In addition, a couplant such as linear and cross-linked high molecular weight polymers, e.g., silicone greases, is employed between the assembled parts or components to cause an ultrasonic coupling effect.

It will of course be realized that various modifications can be made in the design and operation of the present invention without departing from the spirit thereof. Thus, while the principle, preferred construction, and mode of operation of the invention have been explained and what is now considered to represent its best embodiments have been illustrated and described, it should be understood that within the scope of the appended claims the invention may be practiced otherwise than as specifically illustrated and described.

What is claimed and desired to be secured by Letters Patent of the United States is:

1. An ultrasonic inspection system including a holding device for an ultrasonic transducer, said holding device comprising an outer housing including a pair of rectangular-shaped sections including inner surfaces;
   a concave cylindrical recess on the inner surface of each section;
   means for adjoining said sections such that said concave recesses are in opposing relationship;
   a cylindrical shaped bore formed within said adjoined sections;
   an independently rotatable inner housing rotatably retained within said outer housing, said inner housing further comprising and outer cylindrical section rotatably mounted within said outer housing;

an independently rotatable inner cylindrical section rotatably mounted within said outer cylindrical section;

a recess within said inner cylindrical sections for receiving an ultrasonic transducer;

an ultrasonic transducer retained within said inner housing;

retention means for selectively positioning said transducer within said housing; and means for locking said ultrasonic transducer within said inner housing at a selected position.

2. An ultrasonic inspection system including a holding device for an ultrasonic transducer, said holding device comprising:

an outer housing further comprising a pair of cube-shaped sections;

a semi-circular channel in one of said sections;

a hemispherical recess in said other section;

means for adjoining said cube-shaped sections to form a semi-circular bore such that the interior of said hemishperical recess which communicates through said semi-circular bore to the exterior of said adjoined sections;

an inner housing further comprising a ball-shaped section;

a socket-shaped recess within said ball-shaped section for receiving an ultrasonic transducer; and means for selectively positioning said ultrasonic transducer comprising a removal toggle passing through said semi-circular bore and functional engagement with said socket-shaped recess.

3. An ultrasonic inspection system for performing in-service inspection of volume elements of a wall or other structural member comprising:

(a) a remote inspector having a holding device for an ultrasonic transducer, said holding device comprising:

(i) an outer housing further comprising a pair of rectangular-shaped sections including inner surfaces;

a concave cylindrical recess on the inner surface of each section;

means for adjoining said sections such that said concave recesses are in opposing relationship;

a cylindrically-shaped bore formed within said adjoined sections;

(ii) an inner housing rotatably retained within said outer housing further comprising an outer cylindrical section rotatably mounted within said outer housing;

an inner cylindrical section rotatably mounted within said outer cylindrical section;

a recess within said inner cylindrical section for receiving an ultrasonic transducer;

(iii) an ultrasonic transducer retained within said inner housing;

(iv) retention means for selectively positioning said ultrasonic transducer within said inner housing;

(v) means for locking said transducer within said inner housing at a selected position;

(b) positioning means for mounting said holding device on said member and making said holding device to successive positions along a predetermined inspection path on said member;

(c) a control and data acquisition console including connecting means between said holding device and said console for transmitting voltage drive pulses from said console to said holding device and said transducer; and (d) means cooperating with said holding device and said console for obtaining inspection data of volume elements of said member along said predetermined inspection path.

4. (newly added). An ultrasonic inspection system for performing in-service service inspection of volume elements of a wall or other structural member comprising:

(a) a remote inspector having a holding device for an ultrasonic transducer, said holding device comprising:

(i) an outer housing further comprising a pair of tube-shaped sections;

a semi-circular in one of said sections;

a hemispherical recess in said other section;

means for adjoining said tube-shaped sections to form a semi-circular bore such that the interior of said hemispherical recess communicates through said bore to the exterior of said adjoined sections;

an inner housing rotatably retained within said outer housing said inner housing further comprising a rotatable ball-shaped section;

a socket-shaped recess within said ball-shaped section for receiving an ultrasonic transducer;

means for selectively positioning said ultrasonic transducer comprising a removable toggle passing through said semi-circular bore in functional engagement with said socket-shaped recess;

(iii) an ultrasonic transducer retained within said inner housing;

(iv) retention means for selectively positioning said ultrasonic transducer within said inner housing;

(v) means for locking said transducer within said inner housing at a selected position;

(b) positioning means for mounting said holding device on said member and mating said holding device to successive positions along a predetermined inspection path on said member;

(c) a control and data acquisition console including connecting means between said holding device and said console for transmitting voltage drive pulses from said console to said holding device and said transducer; and (d) means cooperating with said holding device and said console for obtaining inspection data of volume elements of said member along said predetermined inspection path.

* * * * *